United States Patent
Thorstensen-Woll

(10) Patent No.: US 10,259,626 B2
(45) Date of Patent: Apr. 16, 2019

(54) CONTAINER SEALING MEMBER WITH PROTECTED SECURITY COMPONENT AND REMOVAL TAB

(71) Applicant: Selig Sealing Products, Inc., Forrest, IL (US)

(72) Inventor: Robert William Thorstensen-Woll, Barrie (CA)

(73) Assignee: Selig Sealing Products, Inc., Forrest, IL (US)

( * ) Notice: Subject to any disclaimer, the term of this patent is extended or adjusted under 35 U.S.C. 154(b) by 146 days.

(21) Appl. No.: 14/383,123

(22) PCT Filed: Mar. 8, 2013

(86) PCT No.: PCT/US2013/029928
§ 371 (c)(1),
(2) Date: Sep. 5, 2014

(87) PCT Pub. No.: WO2013/134665
PCT Pub. Date: Sep. 12, 2013

(65) Prior Publication Data
US 2015/0083723 A1  Mar. 26, 2015

Related U.S. Application Data

(60) Provisional application No. 61/608,383, filed on Mar. 8, 2012.

(51) Int. Cl.
*B65D 51/20* (2006.01)
*B65D 51/22* (2006.01)
*B65D 55/02* (2006.01)

(52) U.S. Cl.
CPC ............. *B65D 51/22* (2013.01); *B65D 51/20* (2013.01); *B65D 55/026* (2013.01)

(58) Field of Classification Search
CPC ....... B65D 51/22; B65D 51/20; B65D 55/026
(Continued)

(56) References Cited

U.S. PATENT DOCUMENTS 4,013,188 A   3/1977  Ray
4,206,165 A   6/1980  Dukess
(Continued)

FOREIGN PATENT DOCUMENTS

AT   501393 A1   8/2006
AT   11738 U1   4/2011
(Continued)

OTHER PUBLICATIONS

International Search Report and Written Opinion of the International Searching Authority from PCT/US2013/029928 dated May 17, 2013, 10 pages.

*Primary Examiner* — Anthony D Stashick
*Assistant Examiner* — James M Van Buskirk
(74) *Attorney, Agent, or Firm* — Fitch, Even, Tabin & Flannery, LLP

(57) ABSTRACT

A sealing member or closure for a container is provided having a protected security component and a removal tab. The sealing member is provided in the form of a one-piece or a two-piece construction and has a tab and an optical security component configured to be protected such that the optical clarity of the security component is maintained after induction sealing.

25 Claims, 6 Drawing Sheets

(58) Field of Classification Search
USPC .......................................... 220/258.3, 259.3
See application file for complete search history.

(56) References Cited

U.S. PATENT DOCUMENTS

| | | | |
|---|---|---|---|
| 4,266,687 A | 5/1981 | Cummings | |
| 4,438,850 A | 3/1984 | Kahn | |
| 4,514,248 A | 4/1985 | Cummings | |
| 4,579,240 A | 4/1986 | Ou-Yang | |
| 4,650,082 A | 3/1987 | Paciorek | |
| 4,741,791 A | 5/1988 | Howard | |
| 4,767,016 A | 8/1988 | Cook, Jr. | |
| 4,837,061 A | 6/1989 | Smits | |
| 4,840,281 A * | 6/1989 | Phillips .............. | B65D 55/026 206/459.1 |
| 4,856,857 A | 8/1989 | Takeuchi | |
| 4,892,209 A | 1/1990 | Dorfman | |
| 4,934,544 A | 6/1990 | Han | |
| 4,961,986 A | 10/1990 | Galda | |
| 4,980,222 A | 12/1990 | Rivera et al. | |
| 4,994,314 A | 2/1991 | Rosenfeld | |
| 5,004,111 A | 4/1991 | McCarthy | |
| 5,015,318 A | 5/1991 | Smits | |
| 5,055,150 A | 10/1991 | Rosenfeld | |
| 5,057,365 A | 10/1991 | Finkelstein | |
| 5,071,710 A | 12/1991 | Smits | |
| 5,084,143 A | 1/1992 | Smith | |
| 5,098,495 A | 3/1992 | Smits | |
| 5,128,779 A | 7/1992 | Mallik | |
| 5,135,262 A | 8/1992 | Smith | |
| 5,149,386 A | 9/1992 | Smits | |
| 5,153,042 A | 10/1992 | Indrelie | |
| 5,160,767 A | 11/1992 | Genske | |
| 5,169,707 A | 12/1992 | Faykish | |
| 5,178,967 A | 1/1993 | Rosenfeld | |
| 5,197,618 A | 3/1993 | Goth | |
| 5,218,472 A | 6/1993 | Jozefowicz | |
| 5,226,281 A | 7/1993 | Han | |
| 5,265,745 A | 11/1993 | Pereyra | |
| 5,319,475 A | 6/1994 | Kay | |
| 5,510,171 A | 4/1996 | Faykish | |
| 5,514,442 A | 5/1996 | Galada et al. | |
| 5,544,770 A | 8/1996 | Travisano | |
| 5,560,989 A | 10/1996 | Han | |
| 5,598,940 A | 2/1997 | Finkelstein | |
| 5,601,200 A | 2/1997 | Finkelstein | |
| 5,615,789 A | 4/1997 | Finkelstein | |
| 5,656,360 A | 8/1997 | Faykish | |
| 5,669,521 A | 9/1997 | Wiening | |
| 5,702,015 A | 12/1997 | Giles | |
| 6,082,566 A | 7/2000 | Yousif | |
| 6,120,882 A | 9/2000 | Faykish | |
| 6,131,754 A | 10/2000 | Smelko | |
| 6,139,931 A | 10/2000 | Finkelstein | |
| 6,194,042 B1 | 2/2001 | Finkelstein | |
| 6,197,396 B1 | 3/2001 | Haas | |
| 6,258,425 B1 | 7/2001 | Parmentier | |
| 6,284,337 B1 | 9/2001 | Lorimor | |
| 6,312,776 B1 | 11/2001 | Finkelstein | |
| 6,351,537 B1 | 2/2002 | Dovgodko | |
| 6,378,715 B1 | 4/2002 | Finkelstein | |
| 6,458,302 B1 | 10/2002 | Shifflet | |
| 6,494,491 B1 | 12/2002 | Zeiter | |
| 6,531,230 B1 | 3/2003 | Weber | |
| 6,602,309 B2 | 8/2003 | Vizulis | |
| 6,659,507 B2 | 12/2003 | Banahan | |
| 6,699,566 B2 | 3/2004 | Zeiter | |
| 6,705,467 B1 | 3/2004 | Kancsar | |
| 6,722,272 B2 | 4/2004 | Jud | |
| 6,737,154 B2 | 5/2004 | Jonza | |
| 6,767,425 B2 | 7/2004 | Meier | |
| 6,775,036 B2 | 8/2004 | Cox | |
| 6,866,926 B1 | 3/2005 | Smelko | |
| 6,902,075 B2 | 6/2005 | OBrien | |
| 6,916,516 B1 | 7/2005 | Gerber | |
| 6,955,736 B2 | 10/2005 | Rosenberger | |
| 6,974,045 B1 | 12/2005 | Trombach | |
| 7,005,178 B2 | 2/2006 | Bonkowski | |
| 7,012,032 B2 | 3/2006 | Cosentino | |
| 7,029,745 B2 | 4/2006 | Bonkowski | |
| 7,064,897 B2 | 6/2006 | Hebrink | |
| 7,128,210 B2 | 10/2006 | Razeti | |
| 7,144,617 B2 | 12/2006 | Schilling | |
| 7,182,475 B2 | 2/2007 | Kramer | |
| 7,224,528 B2 | 5/2007 | Phillips | |
| RE39,790 E | 8/2007 | Fuchs | |
| 7,316,760 B2 | 1/2008 | Nageli | |
| 7,448,153 B2 | 11/2008 | Maliner | |
| 7,531,228 B2 | 5/2009 | Perre | |
| 7,713,605 B2 | 5/2010 | Yousif | |
| 7,740,927 B2 | 6/2010 | Yousif | |
| 7,819,266 B2 | 10/2010 | Ross | |
| 7,838,109 B2 | 11/2010 | Declerck | |
| 8,522,990 B2 | 9/2013 | Thorstensen-Woll | |
| 8,703,265 B2 | 4/2014 | Thorstensen-Woll | |
| 2002/0068140 A1 | 6/2002 | Finkelstein | |
| 2004/0109963 A1 | 6/2004 | Zaggia | |
| 2004/0209028 A1 | 10/2004 | Gosselin | |
| 2005/0048307 A1 | 3/2005 | Schubert | |
| 2005/0208242 A1 | 9/2005 | Smelko | |
| 2006/0000545 A1 | 1/2006 | Nageli | |
| 2006/0003120 A1 | 1/2006 | Nageli | |
| 2006/0003122 A1 | 1/2006 | Nageli | |
| 2006/0124577 A1 | 6/2006 | Ross et al. | |
| 2006/0151415 A1 | 7/2006 | Smelko et al. | |
| 2007/0058227 A1 | 3/2007 | Raksha | |
| 2007/0183047 A1 | 8/2007 | Phillips | |
| 2007/0195392 A1 | 8/2007 | Phillips | |
| 2007/0206249 A1 | 9/2007 | Phillips | |
| 2007/0298273 A1 | 12/2007 | Thies | |
| 2008/0026171 A1 | 1/2008 | Gullick | |
| 2008/0103262 A1 | 5/2008 | Haschke | |
| 2008/0156443 A1 | 7/2008 | Schaefer | |
| 2008/0169286 A1 | 7/2008 | McLean et al. | |
| 2008/0231922 A1* | 9/2008 | Thorstensen-Woll .... | B32B 7/12 359/2 |
| 2008/0233424 A1 | 9/2008 | Thorstensen-Woll | |
| 2008/0257850 A1 | 10/2008 | OKeefe-Broadbent | |
| 2009/0078671 A1 | 3/2009 | Triquet | |
| 2009/0208729 A1 | 8/2009 | Allegaert | |
| 2010/0009162 A1 | 1/2010 | Rothweiler | |
| 2010/0030180 A1 | 2/2010 | Deckerck | |
| 2010/0059942 A1 | 3/2010 | Rothweiler | |
| 2010/0116410 A1 | 5/2010 | Yousif | |
| 2010/0155288 A1 | 6/2010 | Harper | |
| 2010/0170820 A1 | 7/2010 | Leplatois | |
| 2010/0196610 A1* | 8/2010 | Chang ................ | B29C 44/1271 427/379 |
| 2010/0213193 A1 | 8/2010 | Helmlinger | |
| 2010/0221483 A1 | 9/2010 | Gonzalez Carro | |
| 2010/0290663 A1 | 11/2010 | Trassl | |
| 2010/0314278 A1 | 12/2010 | Fonteyne | |
| 2011/0000917 A1 | 1/2011 | Wolters | |
| 2011/0005961 A1 | 1/2011 | Leplatois | |
| 2011/0091715 A1 | 4/2011 | Rakutt | |
| 2012/0070636 A1* | 3/2012 | Thorstensen-Woll ..................... | B65D 77/2032 428/200 |
| 2012/0228297 A1* | 9/2012 | McLean ................ | B32B 27/08 220/270 |

FOREIGN PATENT DOCUMENTS

| | | |
|---|---|---|
| BR | 8200231 U | 9/2003 |
| BR | 0300992 A | 11/2004 |
| DE | 102006030118 B3 | 5/2007 |
| DE | 10204281 A1 | 8/2007 |
| DE | 102007022935 B4 | 4/2009 |
| DE | 202009000245 U1 | 4/2009 |
| EP | 0668221 A1 | 8/1995 |
| EP | 0826598 A2 | 3/1998 |
| EP | 0826599 A2 | 3/1998 |
| EP | 0717710 B1 | 4/1999 |

(56) References Cited

FOREIGN PATENT DOCUMENTS

| | | | |
|---|---|---|---|
| EP | 0915026 | A1 | 5/1999 |
| EP | 0706473 | B1 | 8/1999 |
| EP | 0803445 | B1 | 11/2003 |
| EP | 1834893 | A1 | 9/2007 |
| EP | 1839898 | A1 | 10/2007 |
| EP | 1839899 | A1 | 10/2007 |
| EP | 1857275 | A1 | 11/2007 |
| EP | 1873078 | A1 | 1/2008 |
| EP | 1445209 | B1 | 5/2008 |
| EP | 1918094 | A1 | 5/2008 |
| EP | 1935636 | A1 | 6/2008 |
| EP | 1968020 | A1 | 9/2008 |
| EP | 1992476 | A1 | 11/2008 |
| EP | 2230190 | A1 | 9/2010 |
| EP | 2292524 | A1 | 3/2011 |
| FR | 2754375 | A1 | 4/1998 |
| FR | 2916157 | A1 | 11/2008 |
| FR | 2943322 | A1 | 9/2010 |
| GB | 2241230 | A | 8/1991 |
| GB | 2273492 | A | 6/1994 |
| GB | 2298391 | A | 9/1996 |
| JP | 2004315035 | A | 11/2004 |
| JP | 2000255621 | A | 9/2009 |
| KR | 100711073 | B1 | 4/2007 |
| KR | 100840926 | B1 | 6/2008 |
| KR | 100886955 | B1 | 3/2009 |
| MX | 05002905 | A | 2/2006 |
| MX | 2010001867 | A | 4/2010 |
| TW | 194965 | | 1/1997 |
| WO | 8902402 | A1 | 3/1989 |
| WO | 9308084 | A1 | 4/1993 |
| WO | 9702997 | A1 | 1/1997 |
| WO | 0066450 | A1 | 11/2000 |
| WO | 2005100186 | A1 | 10/2005 |
| WO | 2006018556 | A1 | 2/2006 |
| WO | 2006021291 | A1 | 3/2006 |
| WO | 2006099260 | A1 | 9/2006 |
| WO | 2006108853 | A1 | 10/2006 |
| WO | 2007109113 | A2 | 9/2007 |
| WO | 2008027029 | A2 | 3/2008 |
| WO | 2008027036 | A1 | 3/2008 |
| WO | 2008039350 | A2 | 4/2008 |
| WO | 2008118569 | A2 | 10/2008 |
| WO | 2008125784 | A1 | 10/2008 |
| WO | 2008125785 | A1 | 10/2008 |
| WO | 2008148176 | A1 | 12/2008 |
| WO | 2010115811 | A1 | 10/2010 |
| WO | 2011039067 | A1 | 4/2011 |
| WO | 2012172029 | A1 | 12/2012 |

* cited by examiner

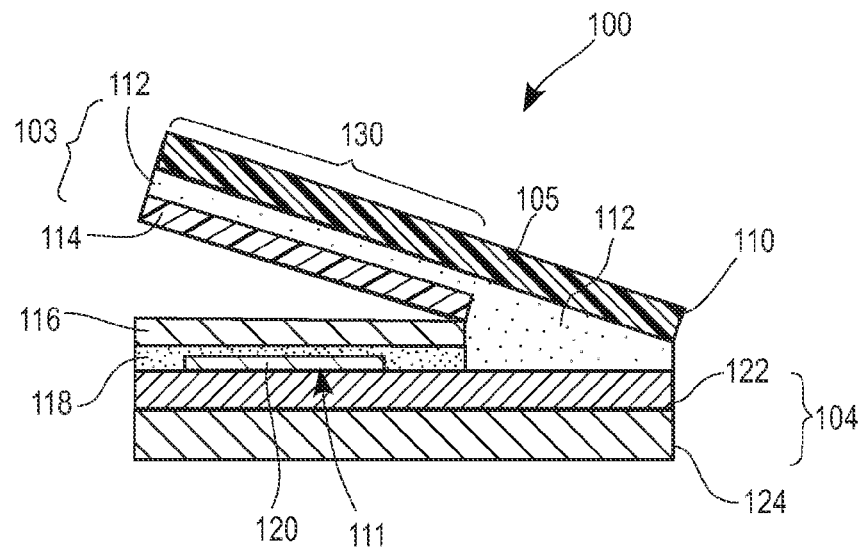
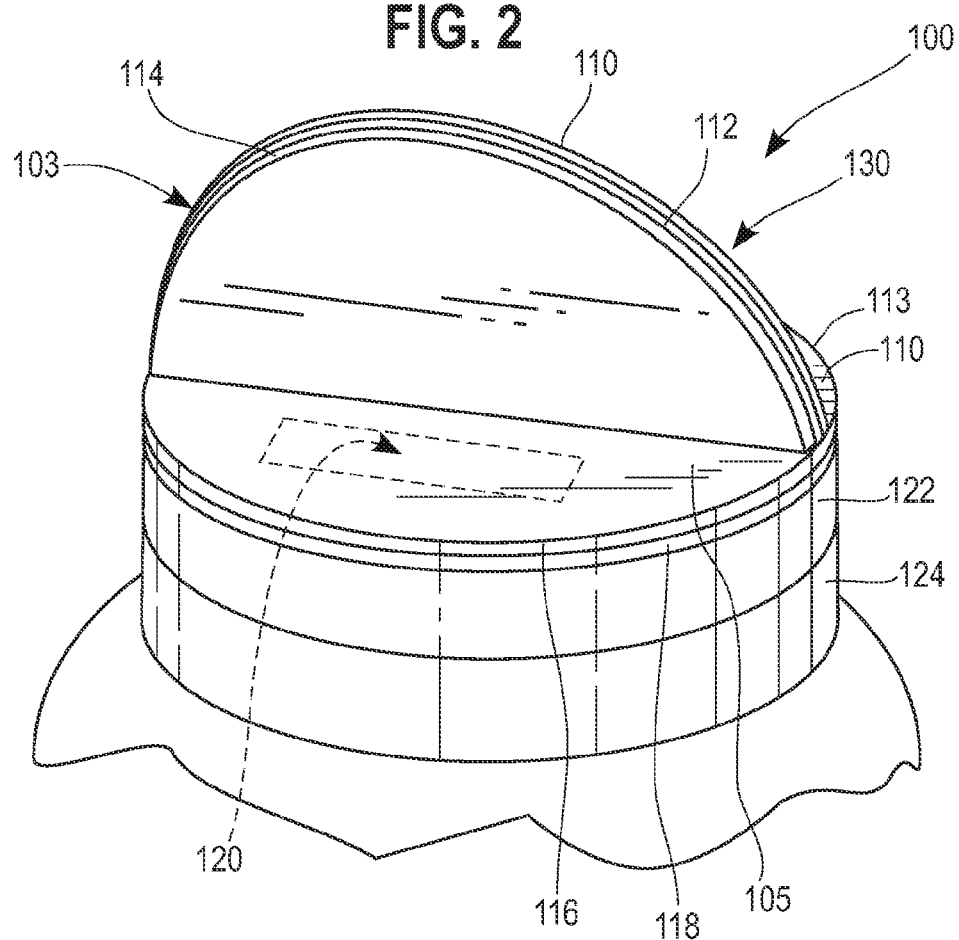

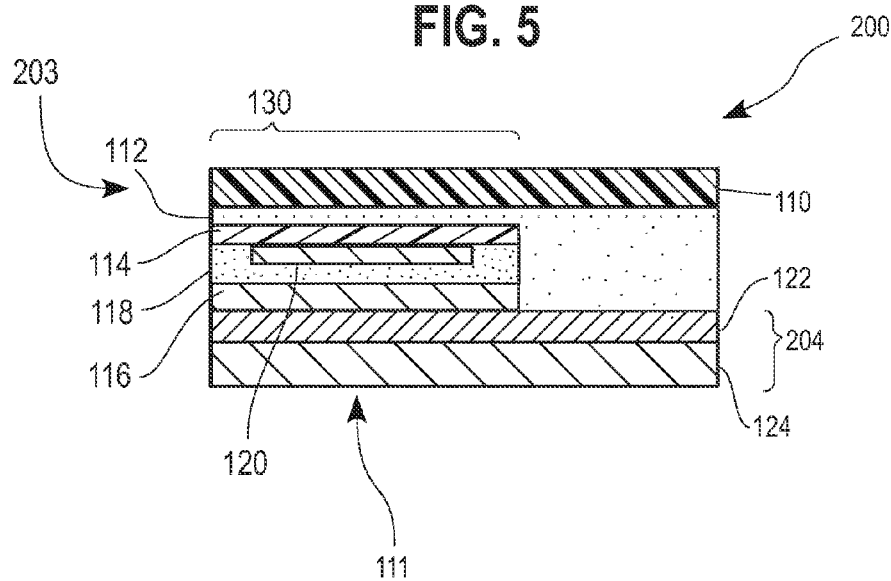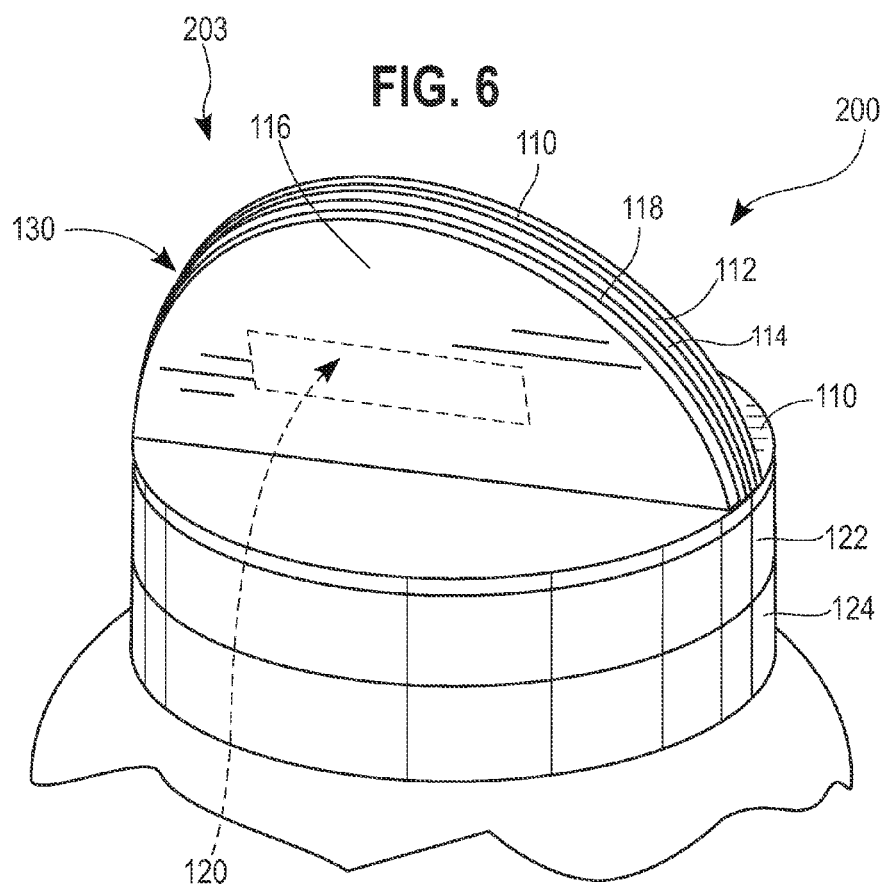

CONTAINER SEALING MEMBER WITH PROTECTED SECURITY COMPONENT AND REMOVAL TAB

CROSS-REFERENCE TO RELATED APPLICATIONS

This application is a U.S. national phase application filed under 35 U.S.C. § 371 of International Application PCT/US2013/029928, filed Mar. 8, 2013, designating the United States, which claims benefit of U.S. Provisional Application No. 61/608,383, filed Mar. 8, 2012, both of which are incorporated herein by reference in their entirety.

FIELD

This disclosure relates to container sealing members, and more particularly to tabbed sealing members having a protected security component.

BACKGROUND

It is common to seal a bottle, jar, or other container with a screw cap and a secondary sealing member across the mouth of the container. Typically, this secondary sealing member can provide evidence of tampering, a vapor barrier or, in some cases, a hermetic seal. In some cases, these secondary sealing members can be provided as a two-piece sealing member with a lower sealing portion and an upper liner portion.

A variety of two-piece sealing members have been developed and have application in the closure industry for use with a screw cap. The cap provides a reclosable closure after the sealing member has been removed by a consumer to gain access to the contents of the container. Often the lower sealing portion includes a heat sensitive sealing layer or bonding layer covered by a metal foil layer. The heat sensitive bonding layer adheres the sealing member to the rim or mouth of a container. The upper liner portion of the sealing member includes a compressing agent (e.g., pulp board, synthetic foam, or the like) that is adjacent the interior of the screw cap and at the opposite end of the sealing member from the heat sensitive sealing layer. There is also generally a release layer, such as a wax layer, adjacent the compressing agent and between the upper liner portion and the lower sealing portion. The release layer is effective to initially hold the upper liner portion to the lower sealing portion to form a unitary or one-piece structure, but the release layer permits the sealing member to separate between these two portions upon cap removal.

In use, the sealing member is inserted into a container or bottle cap at a closure manufacturer as the single or unitary structure where the release layer holds the upper liner portion to the lower sealing portion. The cap generally includes internal threading or other internal retention projections that hold the sealing member against the upper surface of the cap by friction or interference. The cap and sealing member combination may then be provided to an end user that places the cap onto a container mouth where the sealing member is induction sealed to the upper rim of a bottle or container. During induction sealing, an electromagnetic field generated by induction heating equipment heats the metal foil layer in the lower sealing portion to activate the heat sensitive sealing layer for bonding to the rim or mouth of a container. At the same time, the induction heating also causes the release layer to separate the upper liner portion from the lower sealing portion. In the case of the wax layer, the induction heating causes the wax to melt and be absorbed by the compressing agent in the upper liner portion. This converts the one-piece sealing member into two pieces, with the heat sensitive sealing layer bonding the lower sealing portion to the container rim, and the melted wax being absorbed by the compressing agent in the upper liner portion. The compressing agent generally remains lodged in the inner portion of the cap as a cap liner, and the lower sealing member remains adhered to the container when the cap is removed from the bottle by the consumer.

When the cap is removed, the consumer must tear, penetrate, break, or remove the lower sealing portion of the sealing member before the contents of the container may be accessed. The cap may then be screwed back into place on the container neck. Upon removal of the cap, a missing or damaged sealing member can alert the consumer that the contents of the container may have been tampered with prior to purchase.

It is increasingly common to also include an anti-counterfeiting measure along with such sealing members. For instance, such a sealing member can be provided with an optical security feature, such as a hologram, that is visible to the purchaser after the cap is removed. The pattern of the hologram or other optical security feature may be a unique identifier of a particular manufacturer.

BRIEF DESCRIPTION OF THE DRAWINGS

FIG. 1 is a cross-sectional view of exemplary one-piece sealing member having an optical security component and tab;

FIG. 2 is a perspective view of the one-piece sealing member of FIG. 1;

FIG. 5 is a cross-sectional view of another exemplary one-piece sealing member having an optical security component and tab;

FIG. 6 is a perspective view of the one-piece sealing member of FIG. 5;

Figure 3:
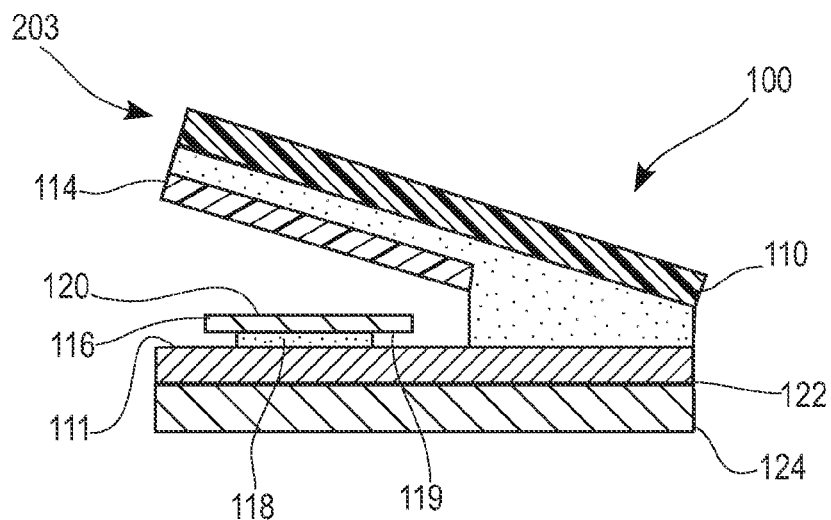
FIG. 3 is a cross-sectional view of another exemplary one-piece sealing member having an optical security component and tab.

Skilled artisans will appreciate that elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the disclosure.

DETAILED DESCRIPTION

A sealing member or closure for a container is described herein. For simplicity, this disclosure generally refers to a container or bottle, but the sealing member may be applied to any type of container, bottle, package or other apparatus having a rim or mouth surrounding an access opening to an internal cavity. In one aspect, the sealing member includes an optical security component and a free tab formed wholly within a perimeter of the sealing member. The optical security component may enable counterfeit products to be identified and also signal, by its condition, when the sealing member has been tampered with.

The sealing members provided herein are configured to protect the optical security component from the induction heating process so that the optical security component can maintain an optical clarity, an optical density, and/or a degree of light reflectance after induction heating similar to that before the induction heating process. In some approaches, the sealing member constructions described herein are effective to protect the optical clarity of the security component from residual wax or other residual components used to releasably bond a liner portion to a seal in a two-piece construction but still permit the optical security component to be visible to a consumer. In other approaches, the sealing member constructions herein may also protect the optical security component from degradation due to the heat generated during the induction heating process. As used herein, optical clarity, optical density, and/or light reflectance are generally used interchangeably and when one is referred to, another can be substituted therefor.

The sealing member may be in the form of a one-piece or a two-piece induction seal and has a tab and an optical security component configured to be protected such that the optical clarity of the security component is maintained after an induction sealing process. The optical security component included in the sealing member can enable counterfeit products to be more readily identified and also signal, by its condition, when the sealing member has been tampered with. For example, the optical security component may be a unique identifier of a particular manufacturer. By one approach, the tab portion of the sealing members described herein is configured to protect the optical clarity of the optical security component from contamination, debris, and/or damage during induction sealing. By one approach, the optical security component may be adhered to a lower surface of the tab. By another approach, the optical security component may be adhered to a seal laminate underneath, and separate from, the tab. By some approaches, the optical security component can comprise a holographic layer.

Conventionally, a prior optical security component would normally be placed as a top layer of a seal in a two-piece construction so that it is visible upon a consumer removing the cap from a container. In this placement, however, the optical security component would be adjacent to and/or contacting a release or wax layer of a two-piece construction that initially holds an upper liner portion to the seal. It was found that a difficulty of constructing a two-piece sealing member in this manner is that a residual quantity of the components from the release layer (such as wax) is often left on the surface of the optical security component after the induction heating process because not all of the release layer components or wax is absorbed by the upper liner portion. Alternatively, in a prior one-piece construction, the optical security component would normally be positioned on the top layer of the seal and adjacent any cap or closure, which could expose the security component to potential scratching, damage, or other degradation.

Because an optical security component, such as a hologram, relies on its visual appearance as an identifier (such as optical clarity, optical density, and/or light reflectance) and/or to achieve its optical characteristics, the presence of residual wax or other residual components and/or thermal or physical damage to the optical security component can alter its appearance or cause the security component to lose a great degree of clarity after induction heating. The presence of wax, other residual components, scratching, and/or other damage can also reduce the effectiveness of the security component in indicating the existence of tampering or counterfeiting. An optical security component that is damaged, has lost optical clarity, or lost a degree of reflectance may suggest to a consumer that the security component is not authentic or has been tampered with.

In this disclosure, use of the terms "upper" and "lower" with respect to surfaces of the sealing member components is in reference to an orientation of the components as generally depicted in FIGS. 1-12 and when the sealing member is in use with a container in an upright position and having an opening at the top of the container. Different approaches to the sealing member will first be generally described, and then more specifics of the various constructions and materials will be explained thereafter.

More specifically, a one-piece or two-piece sealing member is provided as a laminate formed from flexible sheet materials that include a seal with a protected optical security component and tab structure with a free tab. As is described in more detail below, the protected optical security component is bonded to either a lower surface of the free tab or to a seal laminate underneath, and separate from, the free tab. In use, by pulling on a tab, the user can pivot the tab upwardly to expose the optical security component and to remove the sealing member for gaining access to the interior of the container. In either instance, the optical security component and tab are sized and configured to protect the security component from contacting residual wax or other components from the induction heating process when the sealing member is sealed to the rim of a container opening and to otherwise protect the optical security component from damage during handling and assembly of the sealed container.

At least in certain approaches, the seal of the sealing members herein includes a heat sealable layer for bonding to the rim of a container. Above or on top of the heat sealable layer is a membrane or metal layer. The membrane or metal layer may be foil, aluminum, tin, metalized polymers, the like, as well as combinations thereof. The heat sealable layer may include a hot melt adhesive for bonding or securing the seal to the container rim by a heat seal or induction sealing apparatus, which heats the membrane layer and melts the heat sealable layer to bond the seal to the rim of the container. More specifics of the seal are described below.

In one approach and as generally shown in FIGS. 1 through 3, a one-piece tabbed sealing member or seal 100 may include an upper tab structure 103 and a lower seal laminate or lower seal portion 104 that can be bonded to a rim of a container. The lower seal portion 104 may be a laminate or multi-layer sheet including, by one approach, a top layer 122 and a lower heat sealable layer 124 effective to secure the seal member to a container rim during an induction sealing process. The top layer 122 of the seal portion 104 may be a membrane or metal layer or may be other layers as discussed further below. In this approach, the lower seal portion 104 includes the top layer as the membrane or metal layer 122 over and bonded to an upper surface of the lower heat sealable layer 124. In other approaches, the seal portion 104 may also include other layers as needed for a particular application, such as a foamed or non-foamed polymer layer over and bonded to an upper surface of the membrane layer and below the free tab, or other polymer layers between the heat sealable layer 124 and the membrane layer 122.

The tab structure 103 may be a laminate or multi-layer sheet that defines or includes a pull tab or free tab 130. By one approach, the free tab 130 is formed wholly within a circumference or perimeter of the sealing member 100 as generally shown in FIG. 2 depicting the tab 130 pivoted upwardly. The tab structure 103 also may include an upper plastic film layer 110 positioned over and at least partially bonded to the upper layer 122 of the lower seal portion 104 via an adhesive or bonding layer 112 as shown in FIG. 1. The tab structure 103 may also include a tab stock 114 that is bonded to the upper plastic film layer 110 and is adjacent to, but not bonded to, the membrane layer 122 of seal portion 104 to form the tab 130. Tab stock 114 forms the tab 130 because it prevents the upper plastic layer 110 from adhering to the seal portion 104 across at least a portion 130 thereof as generally shown in FIG. 1. The tab structure 103 may also include other polymer layers, such as one or more layers above the upper plastic film layer 110 as needed for a particular application.

By some approaches, the tab stock 114 is a partial layer that extends part-way across the length of the lower seal portion 104. While the relative dimensions of the tab stock 114 are not particularly limited, in some cases the tab stock 114 lies wholly within the circumference of the seal portion 104 and, typically, the tab stock 114 occupies about 25 to about 50 percent of surface area of the sealing member 100. In one aspect, the tab stock 114 is formed of polyester, such as polyethylene terephthalate (PET), or paper. By one optional approach, a lower surface of the tab stock 114 may be coated with a release material, for example silicone. The optional release coating minimizes the possibility that the tab stock 114 will become adhered to lower seal portion 104 during the induction heat sealing process. However, such release coatings are not typically necessary. As shown in at least FIG. 2, the tab stock 114 permits the plastic layer 110 to pivot or hinge upwardly along a boundary line 105 to form the tab 130. By this approach, the tab stock 114 and formed tab 130 are defined wholly within a circumference or perimeter 113 of the sealing member and lower sealing portion thereof.

By one approach and as shown in FIGS. 1-3, the lower seal portion 104 includes an optical security component 120 that is sized and in a position to be protected by the tab 130 but, at the same time, still visible to a consumer in use. As best seen in FIGS. 1 and 3, the optical security component 120 may be positioned below the tab 130 and above membrane layer 122 of the seal portion 104. As shown in FIGS. 1-3, the optical security component 120 can be bonded to the seal portion 104 and, in particular, to an upper surface 111 of the membrane layer 122 (or other upper layer thereof). In one aspect and as shown in FIG. 3, an adhesive layer 118 can be provided on an upper surface 111 of the membrane layer 122 (or other upper layer of the seal portion 104) to bond a lower surface 119 of the optical security component 120 to the membrane layer 122 (or other upper layer of the seal portion). In this aspect, the adhesive layer 118 is sized and configured to not extend beyond a perimeter of the optical security component 120 so that the upper surface 111 does not become adhered to tab stock 114. As such, the adhesive layer 118 may be the same size or smaller than the optical security component 120.

In another aspect and as shown in FIGS. 1 and 2, the optical security component 120 may be further protected (in addition to adhesive layer 118 or in place of adhesive layer 118) by an optional plastic film cover or trapping layer 116 that is adhesively bonded over the security component 120. The trapping layer 116 may also adhesively secure the optical security component 120 to the upper surface 111. A bottom surface of trapping layer 116 may be adhesively bonded by an adhesive layer 118 over the optical security component 120 and to membrane layer 122 as shown in FIG. 1. In this aspect, the security component 120 may be smaller in size than trapping layer 116 (as generally shown in FIG. 2 with the security component 120 shown in phantom lines under the trapping layer) such that the trapping layer 116 extends over the security component 120 with a layer of adhesive 118 to bond the security component 120 to the upper surface of the membrane layer (or other upper layer). In one aspect, there is no adhesive between the bottom surface of the security component 120 and upper surface of membrane layer 122. The trapping layer may be transparent such that the optical security component thereunder is visible to a consumer upon lifting of the tab 130.

Figure 4:
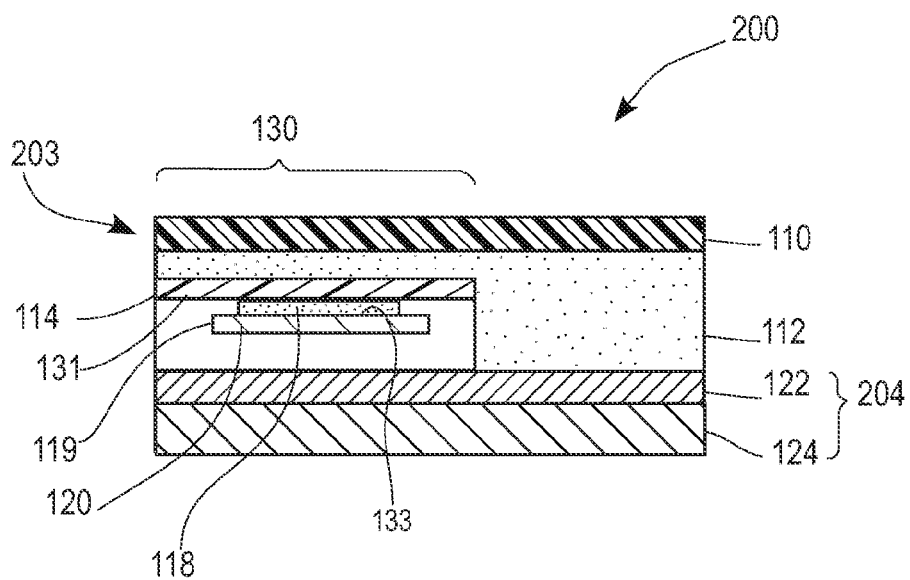
FIG. 4 is a cross-sectional view of another exemplary one-piece sealing member having an optical security component and tab.

By another approach and as generally shown in FIGS. 4 and 5, a sealing member or seal 200 is illustrated showing a tab structure 203 and a lower seal portion 204 with the optical security component 120 bonded to the tab 130 of tab structure 203 and, in particular, to the tab stock 114 so that the optical security component is mounted for movement with the tab 130. Other layers are similar to those of the first approach shown in FIGS. 1-3. The sealing member 200 differs from sealing member 100 of FIG. 1 by the positioning of the optical security component 120 relative to the tab 130 and the lower seal portion 204 of the sealing member.

In one aspect and as shown in FIG. 5, the optical security component 120 in this approach may also include the optional trapping layer 116 to cover and bond the security component to the tab stock 114 of tab 130. Here, the adhesive layer 118 bonds the trapping layer 116 to the lower surface of tab stock 114 and traps the security component 120 against an underside of the tab 130. In one aspect, there is no adhesive between the upper surface of the security component 120 and lower surface of the tab stock. Again, optical security component 120 and tab stock 114 are each of a size and configuration effective to protect the optical security component during induction heating. Such positioning of the optical security component 120 on the lower surface of tab stock 114 tends to block wax or other substances from contacting the security component 120 during induction heating. In this aspect, the security component 120 is smaller in size than trapping layer 116, the tab stock 114, and the tab 130 such that the trapping layer 116 extends over the security component 120 with a layer of adhesive 118 also extending therearound to bond the security component 120 to the tab structure 203.

In another aspect and as shown back in FIG. 4, an adhesive layer 118 can be provided on a bottom surface 131 of the tab stock 114 to bond an upper surface 133 of the optical security component 120 to the tab stock 114. In this aspect, the adhesive layer 118 is sized and configured to not extend beyond an outer perimeter of the optical security component 120 so that the tab stock 114 does not become adhered to the membrane layer 122. As such, the adhesive layer 118 may be the same size or smaller than the optical security component 120 similar to the embodiment of FIG. 3.

In any of the approaches set forth above, the optical security component 120 extends only partially across a length of the sealing member (i.e., less than the entire length of the sealing member) and, in some approaches, has a size and a surface area smaller than the tab 130 and, in some approaches, the tab stock 114. Thus, by one approach, the optical security component 120 can be wholly covered and protected by the tab 130 and/or tab stock 114, but at the same time also be capable of being completely visible to a consumer in use, such as when the tab 130 is pivoted upwardly to expose the security component when the consumer uses the tab to remove the sealing member 100. In one aspect, the optical security component 120 occupies about 25 to about 50 percent of the area under the tab stock 114. In this aspect, the security component 120 is sized to only partially extend across the length of the sealing member and is positioned under tab stock 114 so that security component 120 is wholly protected during induction sealing by the tab 130 and/or the tab stock 114.

Alternatively, the optical security component may be visible to a consumer through the tab 130 and the tab stock 114 because the tab 130, tab stock 114 and any layers thereabove may be translucent or transparent. In one aspect, the optical security component 120 is provided with a thickness of approximately the same thickness as the tab stock 114. For example, the tab stock 114 and the optical security component 120 can be provided with a thickness of about 0.25 to about 0.75 mils each, and in some approaches, each may be about 0.5 mils thick.

The security component 120 can be provided in a variety of shapes and configurations. While shown in FIGS. 2 and 6 as having a rectangular shape, the security component 120 can also be provided as a strip that extends to one or more of the perimeters of the tab stock 114 or membrane layer 122. The security component 120 can also be provided, for example, as a circle, oval, triangle, square, or any other desired shape. Because it is protected, the optical security component remains substantially unchanged after heat sealing. In one aspect, the protection afforded by the sealing members herein aid in the maintenance of the optical clarity of the security components in an induction sealing application. By one approach, the optical density of the optical security components changes less than about 10 percent after heat sealing from an optical density prior to heat sealing. In another aspect, the optical density of the optical security component 120 changes less than about 5 percent after heat sealing as compared to the optical density prior to heat sealing. For example, optical density can be measured by a spectrophotometer or other suitable measuring device.

Figure 7:
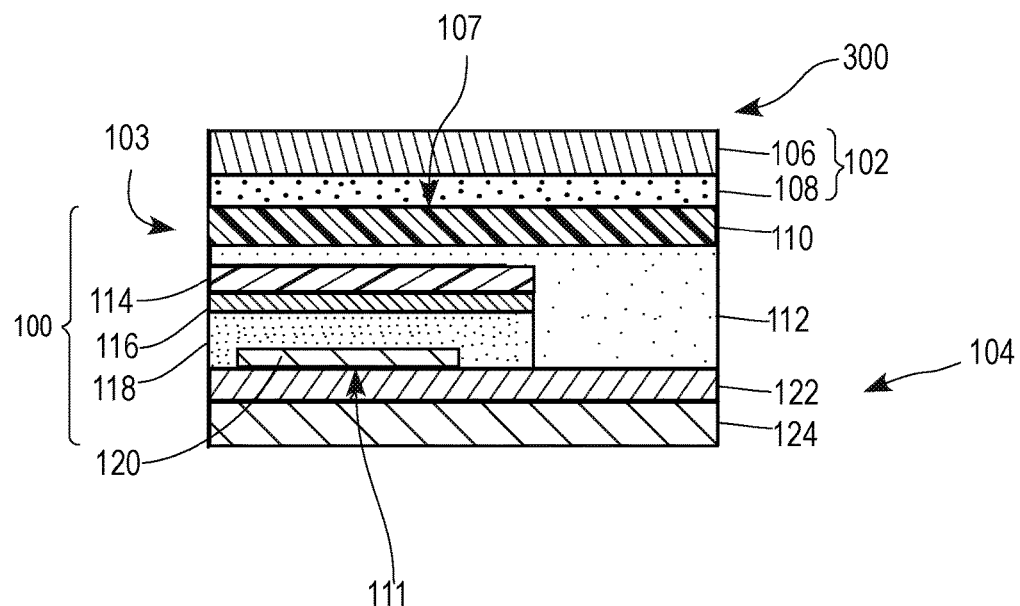
FIG. 7 is a cross-sectional view of an exemplary two-piece sealing member having an optical security component and tab.
Figure 8:
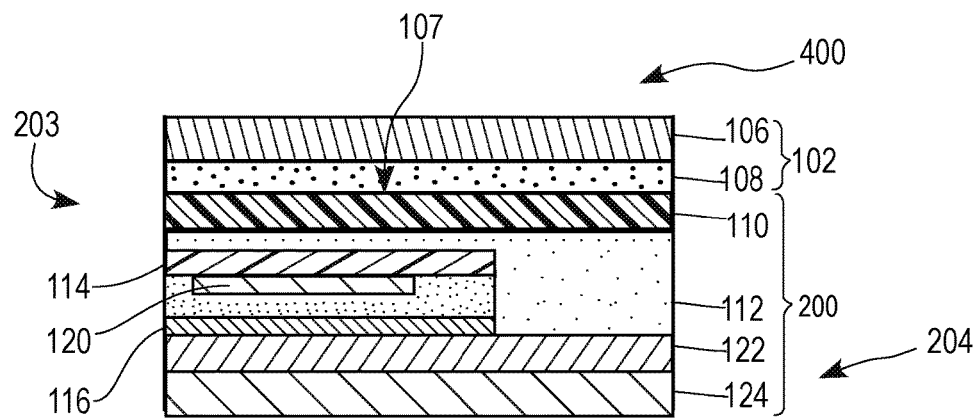
FIG. 8 is a cross-sectional view of another exemplary two-piece sealing member having an optical security component and tab.
Figure 9:
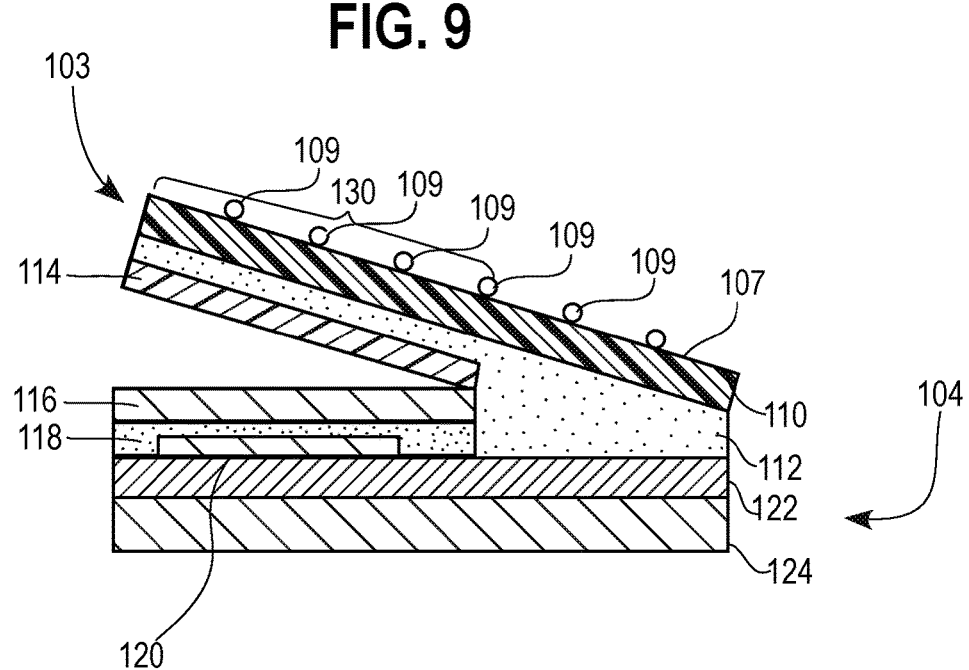
FIG. 9 is a cross-sectional view of an exemplary seal of a sealing member showing residual materials left on an upper surface of the seal after induction sealing.

Turning now to FIGS. 7-9, another example of the sealing member is provided in the form of a two-piece sealing member. In this aspect, the two-piece sealing member is shown as a laminate formed from flexible sheet materials that include a separable upper liner portion and a seal. By some approaches, the seal may include the tab structures 103 and 203 and the lower seal portions 104 and 204 as described in reference to FIGS. 1-6 above. At least in some approaches, the two-piece sealing member also includes the optical security component 120 that is bonded to either the lower surface of the tab or to the lower seal portion underneath, and separate from, the tab as also described above. In either instance, the optical security component and tab are sized and configured to protect the security component from contacting residual wax or other components from the induction heating process when the sealing member is sealed to the rim of a container opening similar to the approaches discussed above.

In a first approach of a two-piece sealing member, FIG. 7 illustrates a cross-sectional side view of a two-piece sealing member 300. The two-piece sealing member 300 includes an upper liner portion 102 combined with seal 100 having the tab structure 103 and the lower seal portion 104 shown in FIG. 1. In a second approach and as shown in FIG. 8, a two-piece sealing member 400 includes an upper liner portion 102 combined with seal 200 having the tab structure 203 and the lower seal portion 204 as shown in FIG. 5. The liner portion 102 and seal 100 or 200 (and associated tab structures) are effective to be separable after induction heating where the upper liner portion 102 remains in a cap and the seal 100 or 200 remains bonded to the rim of a container.

By one approach, the upper liner portion 102 may be a multi-layer structure or sheet including a liner or compressing agent 106 and a release layer 108 that serves to initially bond or hold the compressing agent 106 to an upper surface 107 of the seal 100 or 200, such as a plastic film layer 110 of the tab structure 103 or 203. Upon induction heating, the release layer 108 is activated and allows the upper liner portion 102 to separate from the seal 100 or 200 (and associated tab structure 103 or 203). The upper liner portion 102 is configured to remain in the cap. As described more below, when the release layer is wax, it melts upon induction heating and the molten wax is absorbed by the compressing agent 106. This separation, however, tends to leave residual amounts 109 of the wax or other release layer components on top surface 107 of the seal 100 as generally shown in FIG. 9. This residual wax or other residual components of the release layer can affect the optical clarity, density, and/or the reflectance of the optical security component if the security component is placed in the conventional location on the top surface of the sealing member.

Turning back to FIG. 7, the seal 100 includes an optical security component 120 that is sized and in a position protected from substantial contact with the release layer 108 and/or any residual portions 109 thereof but still capable of being visible to a consumer in use. By one approach, the optical security component 120 is in a position protected from substantial contact with the release layer 108 by being positioned under the tab 130 and/or the tab stock 114 or between the tab and the seal portion 104. By another approach, the optical security component 120 can be bonded to the seal portion 104 and, in particular, to an upper surface 111 of the membrane layer 122 (or other upper layer thereof) as generally shown in FIG. 7. By another approach, the optical security component 120 can be bonded to the tab 130 and, in particular, to the bottom surface of the tab stock 114 as generally shown in FIG. 8. In either approach, the optical security component 120 extends only partially across the length of the sealing member (i.e., less than the entire length of the sealing member) and, in some approaches, has a size and surface area smaller than the tab 130 and, in some approaches, the tab stock 114 similar to the previous embodiments. Thus, the optical security component 120 can be wholly covered and protected by the tab 130 and/or tab stock 114, but at the same time also be capable of being undistorted and visible to a consumer in use, such as when the tab 130 is pivoted upwardly when the consumer uses the tab to remove the sealing member 100. Alternatively, the optical security component may be visible to a consumer through the tab 130 as the tab 130 and any layers thereabove may be translucent or transparent.

By these approaches, the optical security component is substantially protected from coming into contact with wax from wax layer 108 (or other residual components of a release layer 108) during induction sealing by the tab and/or tab stock. In other words, because it is protected, the optical security component 120 remains substantially free of the wax or other components of the release layer after induction sealing but also capable of being visible to a consumer during use. Because it is protected, the optical security component also has a degree of optical clarity and light reflectance that it retains after heat sealing. Because it is protected, the optical security component remains substantially unchanged after heat sealing. In one aspect, the optical density of the optical security components changes less than about 10 percent after heat sealing as compared to an optical density prior to heat sealing. In another aspect, the optical density of the optical security component changes less than about 5 percent after heat sealing as compared to prior to heat sealing.

Figure 10:
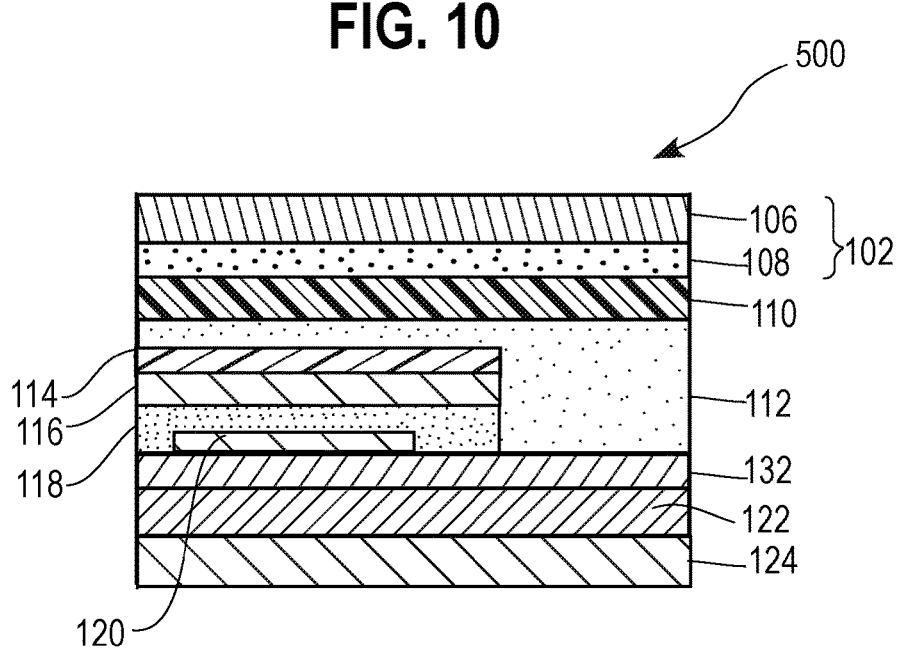
FIG. 10 is a cross-sectional view of an exemplary two-piece sealing member having an optical security component and tab.

FIG. 10 illustrates a cross-sectional side view of a further approach to a sealing member 500 having an optical security component and a free tab. Here, sealing member 500 is similar to sealing member 300 of FIG. 7 but further includes an additional layer 132 on top of the membrane layer 122. Although not shown in the drawings, it is further contemplated that sealing member 400 of FIG. 8 could also include the additional layer 132 on the upper surface of metal layer 122. Likewise, the sealing members of FIGS. 1-6 may also include the additional layer 132.

By one approach, the additional layer 132 may be a foamed or non-foamed polymer layer such as a polyolefin, for example, polyethylene. The layer can be included to provide structural integrity and/or heat redistribution to the sealing member during induction heating in view of the uneven cross-sectional thicknesses between the tabbed (and hologram insertion) and non-tabbed sides of the seal. A foam layer can also be effective to provide a cushioning effect such that the pressure exerted and heat applied around the circumference of the laminate is equalized. Particularly, the effect of the difference in thickness of the tabbed portion, which includes the optical security component and optical cover film or trapping layer, compared to the non-tabbed portion can be minimized so that a more uniform bond can be formed around the circumference of the sealing member. An additional advantage is that foam can act as an insulating and/or heat redistribution layer during induction sealing and thereby limit the amount of heat that reaches the wax layer and the security component so that the wax layer melts evenly between both sides of the seal but reduces the risk of burning the compressing agent. In some approaches, the foam has a density of about 0.6 to about 0.9 g/cc. The additional layer 132 may also be a non-foamed layer, such as a non-foamed polymer layer having a density and thickness effective to provide a sufficient bond to the container with sufficient amounts of heat penetrating the seal to melt the wax layer at the same time. By one approach, the non-foam polymer layer may have a density of about 0.96 g/cc to about 0.99 g/cc and a thickness of about 2 to about 10 mils.

Now that the basic structures of various one-piece and two-piece sealing members with protected optical security components are set forth above, further details about the various layers and components of the sealing members are described in more detail.

The optical security component 120 can include a variety of optical layers, materials, or components that are useful as anti-counterfeiting security devices. The type of optical security component is not particularly limited, but generally includes security components that rely on optical or light reflecting effects to signify authenticity. In one aspect, the security materials used are generally of the type that are susceptible to degradation or reduction in optical clarity by the presence of residual wax or other residual substances of the release layer 108 or which may be degraded as a result of the induction sealing process. Suitable security components can include a variety of optical security features including, for example, holographic layers, optically variable inks, color-shifting inks, interference films, visible microprinting, and combinations thereof. The security component can be provided by one layer or two more layers adhered together. By one approach, the optical security component may include a holographic component comprising an embossed image layer having an upper plastic film layer or PET bonded to a first or upper surface of the image layer and a metal layer on a second or lower surface of the embossed image layer. In another approach, the optional trapping layer 116 may also provide the plastic film layer of the hologram.

As described above, the optical security component 120 is positioned to be protected from residual wax or other residual components of the release layer 108 that may be left on the lower seal portion 104 after induction heating. Due to this protection, the optical security component 120 retains a degree of optical clarity and/or light reflectance after induction sealing that it had before induction sealing. In one aspect, the optical density of the optical security components changes less than about 10 percent after heat sealing. In another aspect, the optical density of the optical security component changes less than about 5 percent after heat sealing.

The liner or compressing agent 106 can be formed of one or more layers of cardboard, pulp board, or a synthetic compressing agent (such as a synthetic foam or synthetic fibers) that is effective for absorbing the release layer 108 upon induction heating. In one approach, the compressing agent 106 may include a layer of foamed plastic material to which a paper layer (not shown) has been adhered to a bottom surface thereof. In this approach, the paper layer is the layer in contact with the release layer 108 for absorbing the molten wax or other components thereof. By another approach, the liner or compressing agent has a thickness in the range from about 400 to about 1800 μm. Synthetic foam or fibers useful herein include materials with a suitable compression factor comparable to pulp board of the type traditionally used in induction seals. For example, low density polyethylene (LDPE), coextruded LDPE, polypropylene (PP), and polystyrene (PS) foam or fibers may also be used as the compression agent. The synthetic material selected should have a sufficient absorbency, suitable pore volume, and structure to absorb substantially all of the wax used in the seal. The dimensions of the compressing agent absorbing material will vary according to the application and the size of the opening of the container and size and construction of the closure being used.

By one approach, the release layer 108 may be a wax layer. The wax may include any suitable wax material which will melt within the temperature range to which the sealing member is to be subjected by an energy source during the induction sealing process. For example, the wax layer may include a blend of paraffin and microcrystalline waxes. By one approach, the wax layer may comprise a blend of paraffin wax and microcrystalline wax wherein the proportion of microcrystalline wax used in the wax layer is adjusted to provide a wax layer formulated to improve absorption of the wax by the compressing agent. Alternatively, the wax layer may include microcrystalline wax modified with other polymeric additives to enhance its initial bonding properties. For instance, the wax layer may comprise microcrystalline wax and at least one of ethylene vinyl acetate and polyisobutylene.

In general, the application of induction energy to the sealing member heats the polymeric sealable layer 124 to a temperature in the range from about 300 to about 450° F. The volume or thickness of the wax layer, therefore, should be selected such that substantially all of the wax will melt during the manufacturing process and be absorbed by the compressing agent.

Suitable hot melt adhesives or sealants for the heat sealable layer 124 include, but are not limited to, polyesters, polyolefins, ethylene vinyl acetate, ethylene-acrylic acid copolymers, surlyn, and other suitable materials. By one approach, the heat sealable layer may be a single layer or a multi-layer structure about 0.2 to about 3 mils thick.

The membrane layer 122 may be a metal layer, such as, for example, aluminum foil. In one aspect, the metal layer may be about 0.3 to about 2 mils thick. The membrane layer may also be foil, tin, metalized polymers, and the like, as well as combinations thereof.

The adhesives useful for the adhesive layers described herein include, for example, ethylene vinyl acetate (EVA), polyolefins, and 2-component polyurethane. If the tab stock includes any printing, the adhesive should be transparent so that the printing is visible through the adhesive.

The upper plastic film layer 110, tab stock 114, and the trapping layer 116 can be selected from a variety of suitable plastic materials. The tab stock 114 can also be a paper material, such as paper, cellulose, wax paper, and the like. For example, the plastic film can be selected from the group consisting of polyester, preferably polyethylene terephthalate, polyamide, polypropylene, or a combination thereof. In one approach, the plastic film cover or trapping layer 116 should be transparent so that the security component can be visible to the end user. Preferably the thickness of the plastic film layer 110 is in the range from about 0.5 to about 3 microns. The plastic film cover has a thickness of about 0.5 to about 3 microns.

In use, the sealing member can be cut into appropriately sized disks to form a vessel closing assembly. The sealing member is inserted into a screw cap or other closure which, in turn, is applied to the neck of a container to be sealed. The screw cap can be screwed on to the open neck of the container, thus sandwiching the sealing member between the open neck of the container and the top of the cap. Heat is then applied to seal the bottom subassembly of layers forming the seal portion to the neck of the container. The applied heat causes the wax layer to melt and the molten wax is absorbed by the compressing agent of the liner layer. As such, at this stage of processing the wax is no longer present as a separate adhesive layer and the seal portion and liner portion are no longer adhered to one another. Therefore, the sealing member can be adhered to the screw cap without concern for ripping the seal upon opening because the bond between the seal and liner is no longer present. Upon twisting the screw cap, the two piece sealing member will separate between the plastic film layer 110 and the compressing agent 106 without requiring significant force. The compressing agent 106 which has absorbed the wax layer will remain in the cap and the seal will remain adhered to the neck of the container. With the optical security component 120 protected from fouling or contact by any residual wax, the optical clarity, optical density, and/or reflectance of the security component is maintained after the induction heating process as described above.

In some approaches, the sealing member is configured to tear across a major surface thereof upon pulling of the tab. Another advantage of the optical security components 120 described herein is that they extend only partly across the sealing member. Thus, the sealing member, if desired, can retain an ability to tear upon sealing member removal without accompanying tearing of the optical security component. That is, the membrane 122 and heat sealable layers 124 in some applications can tear across a portion thereof, in use, when the tab is pulled upwards. If the optical security component 120 extended across the entire sealing member, it would tend to increase the tear strength of the seal portion, generally due to the construction of the security component, such that it would be much more difficult for a consumer to remove the sealing member.

Figure 11:
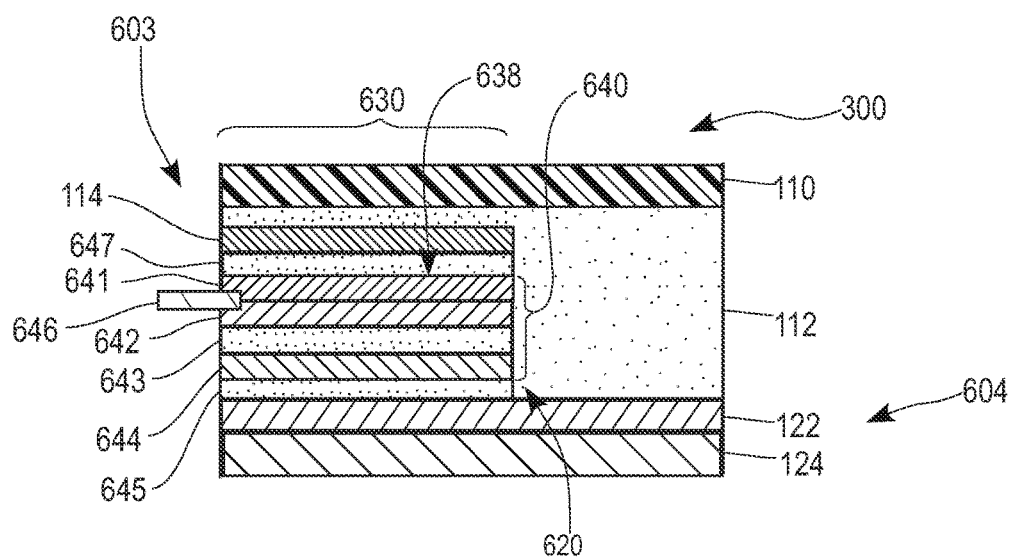
FIGS. 11 and 12 are cross-sectional views of another exemplary sealing member having a hologram as the optical security component with a splitting point in the hologram.
Figure 12:
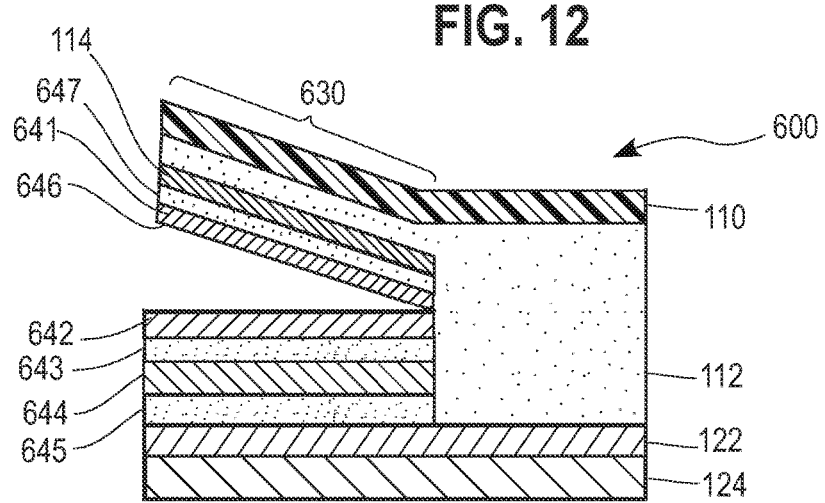

In yet another approach, a sealing member 600 is provided with an optical security component 620 as shown in FIGS. 11 and 12 having a splitting point 638 configured therein to form a tab 630 upon splitting of the security component 620. In this approach, the security component 620 includes a holographic film 640 having a PET layer 641 bonded to an embossed image layer 642 which bears a holographic image and which is bonded to a metal substrate 644, such as, for example, aluminum, by adhesive layer 643. The hologram is bonded to membrane layer 122 (or other layer of the lower seal portion 604) by an adhesive layer 645 and at the same time bonded to the tab stock 114 by an adhesive layer 607. Thus, the tab 130 is initially adhered to both the lower seal portion 604 and the tab structure 603.

The PET layer 641 and the embossed image layer 642 of the hologram are bonded together in such a manner, and with such a bonding strength, that the layers 641 and 642 are separable from each other at a splitting point 638. In other words, the bond at the splitting point 638 is not as strong as the bond formed by the embossed layer 642 and metal substrate 644 to membrane layer 122. The PET layer 641 and embossed image layer 642 can be split or separated by the user at notch, member, other release point represented as 606. Accordingly, a tab 630 is formed by the tab stock 114, adhesive layer 647, and PET layer 641 only after a user pulls upwardly at the notch or release point 646 because the sealing member 600 partially splits apart at splitting point 638 and uppermost layers 110, 112, 114, 641, and 647 of the sealing member are pulled away to expose the lower layers of the hologram 640, which is visible in the embossed image layer 642 that remains bonded to the lower seal portion and membrane 122 (or other upper layer). Separation of the initially-bonded-together hologram 640 forms the tab 630. The user can continue to pull the tab 630 to remove the remainder of the sealing member from the container. By pulling on the tab 630, the seal 600 is configured to be removed from a container in one piece, or alternatively, the lower layers below the tab may be configured to tear.

While not shown in the drawings, the configuration of the hologram 640 can be reversed so that the embossed image layer is bonded to the underside of the tab stock 114. By this approach, the order of layers 641 to 644 is reversed such that tab stock 114 is bonded to metallic substrate 644 by adhesive 647 and PET layer 641 is bonded to membrane layer 122 or other layer of the lower seal portion by adhesive layer 645. Accordingly, when a tab 630 formed by tab stock 114, adhesive layer 647, metal substrate 644, and embossed image layer 642 is pulled upwardly, all of the uppermost layers 110, 112, 114, 642, 644, and 647 of the sealing member are pulled away to expose the hologram visible in the embossed image layer 642 on the underside of the tab. The user can continue to pull the tab away to remove the remainder of the sealing member from the container.

The bonding of the PET layer 641 to the embossed image layer 642 is carefully controlled to set the amount of adhesion that exists between the PET layer 641 and the embossed image layer 642 to allow for the splitting. For example, PET holographic film produced by American Bank Note Holographics (ABNH) may be used. Alternatively, a holographic product could be designed that would function in the same manner if the holographic film was modified to contain some type of release layer between the PET film layer 641 and the embossed image layer 642.

It will be understood that various changes in the details, materials, and arrange-ments of the seal laminate, which have been herein described and illustrated in order to explain the nature of the seals described herein, may be made by those skilled in the art within the principle and scope of the embodied description.

What is claimed is:

1. A two-piece sealing member for a container having an opening surrounded by a rim, the sealing member comprising:
    a liner portion and a seal, the liner portion and the seal effective to be separable after induction heating so that the liner portion remains in a cap of a container and the seal remains adhered to a rim of a container;
    a wax layer on a lower surface of the liner portion releasably bonding the liner portion to an upper surface of the seal;
    a tab structure of the seal defining a tab lying wholly within the circumference of the sealing member and extending part way across the seal, the tab can be pulled, in use, to remove the seal from a container;
    a lower laminate having a top layer under the tab structure and a heat sealable layer effective to secure the seal to a container during induction sealing; and
    an optical security component located under the tab, the optical security component and the tab each of a size and configuration effective to protect the optical security component from contact with the wax during induction heating and arranged so that the optical security component is visible upon pivoting of the tab, wherein the optical security component has an optical density after induction sealing within about 10 percent of an optical density prior to induction sealing.

2. The two-piece sealing member of claim 1, wherein the optical security component is bonded to a first portion of the top layer.

3. The two-piece sealing member of claim 1, wherein the optical security component is bonded to the tab.

4. The two-piece sealing member of claim 1, further comprising a polymer layer above the top layer and under the tab structure and wherein the optical security component is bonded to the polymer layer.

5. The two-piece sealing member of claim 4, wherein the polymer layer is selected from the group consisting of a non-foamed polymer layer and a foamed polymer layer.

6. The two-piece sealing member of claim 1, wherein the optical security component includes a security feature selected from the group consisting of a holographic component, optically variable ink, color shifting ink, interference films, and combinations of holographic components and optically variable ink and color shifting ink and interference films.

7. The two-piece sealing member of claim 1, wherein the optical security component includes a holographic portion with an embossed image layer having a plastic film layer bonded to a first surface of the image layer and a metal layer on a second surface of the embossed image layer.

8. The two-piece sealing member of claim 1, wherein the optical security component is bonded to both the tab stock and the membrane layer and includes a splitting point therein effective to form the tab upon the optical security component splitting apart at the splitting point.

9. A two-piece sealing member for a container having an opening surrounded by a rim, the sealing member comprising:
    a liner portion and a seal, the liner portion and the seal effective to be separable after induction heating so that the liner portion remains in a cap of a container and the seal remains adhered to a rim of a container;
    a wax layer on a lower surface of the liner portion releasably bonding the liner portion to an upper surface of the seal;
    a tab structure of the seal defining a tab lying wholly within the circumference of the sealing member and extending part way across the seal, the tab can be pulled, in use, to remove the seal from a container;
    a lower laminate having a top layer under the tab structure and a heat sealable layer effective to secure the seal to a container during induction sealing; and
    an optical security component located under the tab, the optical security component formed by at least one layer extending only part way across the seal, the optical security component being smaller than the tab such that the tab is effective to protect the optical security component from contact with the wax during induction heating.

10. The two-piece sealing member of claim 9, wherein the optical security component is bonded to a first portion of the top layer.

11. The two-piece sealing member of claim 9, wherein the optical security component is bonded to the tab.

12. The two-piece sealing member of claim 9, further comprising a polymer layer above the top layer and under the tab structure and wherein the optical security component is bonded to the polymer layer.

13. The two-piece sealing member of claim 12, wherein the polymer layer is selected from the group consisting of a non-foamed polymer layer and a foamed polymer layer.

14. The two-piece sealing member of claim 9, wherein the optical security component includes a security feature selected from the group consisting of a holographic component, optically variable ink, color shifting ink, interference films, and combinations of holographic components and optically variable ink and color shifting ink and interference films.

15. The two-piece sealing member of claim 9, wherein the optical security component includes a holographic portion with an embossed image layer having a plastic film layer bonded to a first surface of the image layer and a metal layer on a second surface of the embossed image layer.

16. The two-piece sealing member of claim 9, wherein the optical security component has an optical density after induction sealing within about 10 percent of an optical density prior to induction sealing.

17. The two-piece sealing member of claim 9, wherein the optical security component is bonded to both the tab stock and the membrane layer and includes a splitting point therein effective to form the tab upon the optical security component splitting apart at the splitting point.

18. A two-piece sealing member for a container having an opening surrounded by a rim, the sealing member comprising:
- a liner portion and a seal, the liner portion and the seal effective to be separable after induction heating so that the liner portion remains in a cap of a container and the seal remains adhered to a rim of a container;
- a wax layer on a lower surface of the liner portion releasably bonding the liner portion to an upper surface of the seal;
- a tab structure of the seal defining a tab lying wholly within the circumference of the sealing member and extending part way across the seal, the tab can be pulled, in use, to remove the seal from a container;
- a lower laminate having a top layer under the tab structure and a heat sealable layer effective to secure the seal to a container during induction sealing; and
- an optical security component located under the tab and being visible through the tab, the optical security component and the tab each of a size and configuration effective to protect the optical security component from contact with the wax during induction heating,
- wherein the optical security component has an optical density after induction sealing within about 10 percent of an optical density prior to induction sealing.

19. The two-piece sealing member of claim 18, wherein the optical security component is bonded to a first portion of the top layer.

20. The two-piece sealing member of claim 18, wherein the optical security component is bonded to the tab.

21. The two-piece sealing member of claim 18, further comprising a polymer layer above the top layer and under the tab structure and wherein the optical security component is bonded to the polymer layer.

22. The two-piece sealing member of claim 21, wherein the polymer layer is selected from the group consisting of a non-foamed polymer layer and a foamed polymer layer.

23. The two-piece sealing member of claim 18, wherein the optical security component includes a security feature selected from the group consisting of a holographic component, optically variable ink, color shifting ink, interference films, and combinations of holographic components and optically variable ink and color shifting ink and interference films.

24. The two-piece sealing member of claim 18, wherein the optical security component includes a holographic portion with an embossed image layer having a plastic film layer bonded to a first surface of the image layer and a metal layer on a second surface of the embossed image layer.

25. The two-piece sealing member of claim 18, wherein the optical security component is bonded to both the tab stock and the membrane layer and includes a splitting point therein effective to form the tab upon the optical security component splitting apart at the splitting point.

* * * * *